United States Patent [19]

Cropsey

[11] 4,326,505
[45] Apr. 27, 1982

[54] SURGICAL PROCEDURE FOR EMBRYO TRANSPLANTS ON ANIMALS

[75] Inventor: Leo M. Cropsey, Golden, Colo.

[73] Assignee: Occidental Petroleum Corporation, Los Angeles, Calif.

[21] Appl. No.: 109,802

[22] Filed: Jan. 7, 1980

[51] Int. Cl.³ .............................................. A61B 19/00
[52] U.S. Cl. .................................................... 128/1 R
[58] Field of Search ........................................ 128/1 R

[56] References Cited

U.S. PATENT DOCUMENTS 3,854,470  12/1974  Augspurger ........................ 128/1 R

OTHER PUBLICATIONS

Bedirian, K. N. & Baker, R. D. (1973) An Intravaginal Method for the Recovery and Transfer of Bovine Eggs, Con. J. Anim. Sci., pp. 67–69.
Embryo Transfer in Farm Animals, Monograph No. 16, 1977, cover page, title and copyright page, pp. 10–13 and 27–30, 40.

Primary Examiner—Stephen C. Pellegrino
Attorney, Agent, or Firm—Christie, Parker & Hale

[57] ABSTRACT

A method is disclosed for implanting an embryo transplant from a donor mammal into the uterus of a recipient mammal. The method comprises making an incision in the lateral wall of the vagina of a recipient mammal posterior of the cervix. The uterine horn leading to an ovary having a corpus luteum thereon is positioned in proximity to the incision in the vaginal wall. The wall of the uterine horn is exposed through the incision in the vaginal wall. A hole is punctured through the exposed wall of the uterine horn. A cannula is inserted through the incision in the vaginal wall and through the hole in the wall of the uterine horn. The embryo transplant to be implanted in the recipient mammal is introduced through the cannula into the lumen of the uterine horn. After insertion of the embryo the cannula is withdrawn.

19 Claims, 2 Drawing Figures

SURGICAL PROCEDURE FOR EMBRYO TRANSPLANTS ON ANIMALS

BACKGROUND OF THE INVENTION

The method herein relates to implanting an embryo transplant from a donor mammal into the uterus of a recipient mammal.

More particularly, the method herein relates to a method for implanting an embryo transplant from a donor mammal into the uterus of a recipient mammal by surgical techniques for limiting damage to the reproductive tract and other body tissues of the recipient mammal generally incurred by present surgical techniques and inhibiting the likelihood of abortion of the implanted embryo from the uterus.

Current methods of implanting embryos into host animals during the estrus cycle for such host animal to carry the embryo through the normal gestation period include using surgical and nonsurgical techniques. For example, nonsurgical techniques of implanting embryos into host animals are performed by inserting a catheter through the vagina and into the uterus of the animal. The catheter serves as a conduit through which the embryo is transferred into the uterus. The catheter is inserted through the vagina, through the cervix and into the uterus. Once the catheter is past the cervix, it is manipulated by the end extending from the vagina to extend the catherter into a uterine horn of the uterus. The uterine horn in which the catheter is placed leads to an ovary on which a corpus luteum is formed. Such a nonsurgical technique is undesirable. The passing of the catheter through the cervix can damage the cervix. Additionally, the cervix can be damaged when the catheter is being manipulated to position the catheter into the proper uterine horn. The endometrium of a mammal is also easily damaged during post-estrus as the tissue comprising the cervix and endometrium is readily subject to hemorrhage. It is desirable to prevent physical damage to the cervix and endometrium as the condition of the cervix and endometrium is integral to inhibiting abortion of an embryo during gestation.

Current surgical techniques for implanting embryos into the uterus of recipient mammals generally comprise anesthetizing the animal and performing ventral abdominal or lumbar regional surgery on the animal to locate the uterine horn in which to implant the embryo. Such surgery requires the making of an incision through the walls of body tissue and generally requires total anesthetizing of the animal. This procedure is undesirable in the bovine species as they do not tolerate such total anesthetization and can die from the anesthesia. The procedure is also expensive, time consuming and is difficult to perform other than in an equipped operating room. Additionally, there is a possibility of infection to the recipient mammal as the peritoneal cavity is opened. Also, with such surgery, there occurs postoperative adhesions on the incised tissue which makes multiple transplants to the same recipient mammal difficult and sometimes ineffective in producing a sustainable gestation period. Such adhesions do not have the elasticity of normal tissue. The adhesions form after each surgical operation. With the build up of adhesions, it is generally recommended that each recipient animal function as recipient for only a few transplants in order to maintain viability of the embryo throughout the gestation period. It is desirable to provide a method of implanting embryos that would reduce the difficulties and drawbacks of the current surgical methods and would improve the likelihood of the recipient mammal retaining the embryo through a normal gestation period.

SUMMARY OF THE INVENTION

The method herein is directed to implanting an embryo transplant from a donor mammal into the uterus of a recipient mammal. In particular, the method herein is directed to implanting an embryo transplant from a donor mammal into the uterus of a recipient mammal while preventing damage to the reproductive tract and adjacent body tissues and thereby inhibiting the likelihood of abortion of the implanted embryo.

The method for implanting an embryo transplant from a donor mammal into the uterus of a recipient mammal comprises the steps of making an incision in the lateral wall of the vagina of the recipient mammal. The incision is made in the vaginal wall lateral and posterior to the cervix, i.e., between the cervix and the external orifice of the genital canal. The incision in the vaginal wall can be a slit incision or a circular incision. Generally, it is preferred that the incision be no more than about ¾ of an inch in length. Such a size of the incision or opening is preferrred as it is sufficiently large to enable a cannula to be inserted therethrough, yet is sufficiently small as to be self-healing without the need of suturing.

The uterine horn leading to an ovary, having a corpus luteum thereon, is positioned in proximity to the incision in the vaginal wall. The uterine horn is positioned to expose the wall of the uterine horn, myometrium, through the vaginal incision. In larger mammals the uterine horn can be positioned proximate to the incision by rectal palpation of the uterus and uterine horn. The corpus luteum provides a globular mass which can be distinguished by palpation. Upon ascertaining the uterine horn leading to the ovary having a corpus luteum, that uterine horn is manipulated, manually or with instruments, to position the uterine horn proximate to the vaginal incision.

A hole is punctured through the exposed wall of the uterine horn by puncturing the hole through the opening provided on the vaginal wall by the incision. After a hole has been punctured through the wall of the uterine horn and opening into the lumen of the uterine horn, a cannula is inserted through the incision in the vaginal wall, through the hole in the wall of the uterine horn and into the lumen of the uterine horn. The embryo transplant is then introduced into the lumen of the uterine horn through the cannula. After introducing the embryo transplant into the lumen, the cannula is withdrawn. The uterine horn then returns to its normal location. The incision in the vaginal wall and hole in the uterine horn heal in time. The cervix and the bulk of the endometrium remain substantially unaffected by the implanting method herein.

The method herein can be practiced in regard to most mammals, including humans, and in particular, can be performed on agricultural animals such as cattle, horses, sheep and hogs and on domestic animals such as dogs and cats.

BRIEF DESCRIPTION OF THE DRAWING

For a better understanding of the method herein reference can be made to the accompanying drawings wherein.

DETAILED DESCRIPTION OF THE INVENTION

Figure 1:
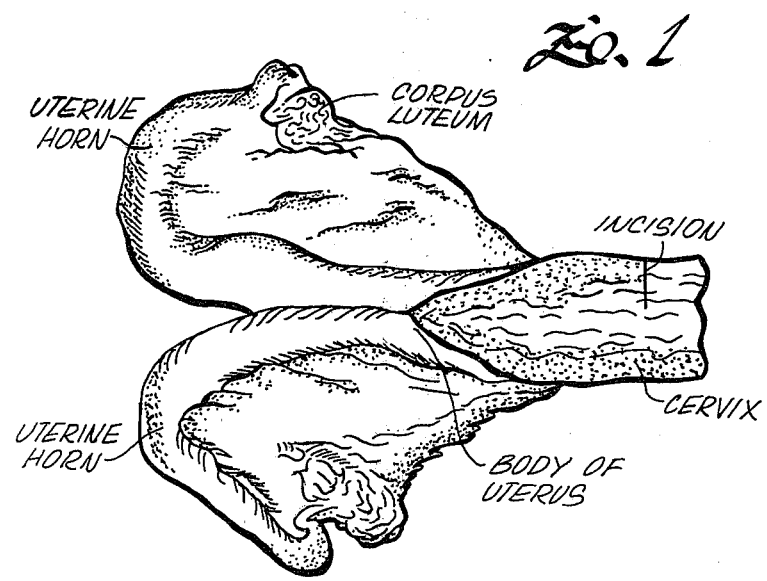
FIG. 1 schematically illustrates the uterus and surrounding related reproductive organs of a cow.
Figure 2:
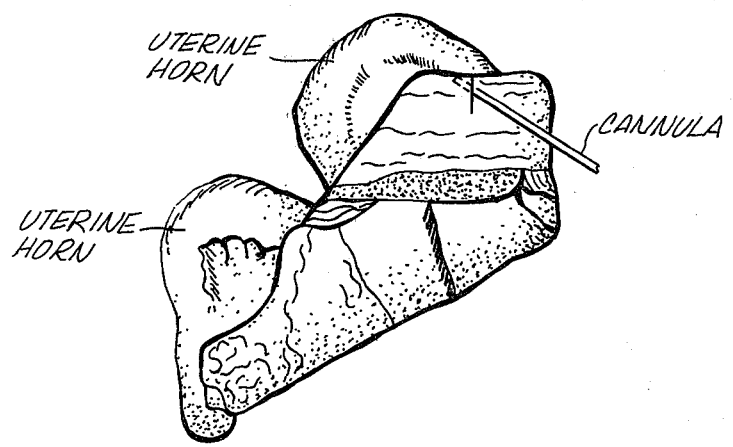
FIG. 2 schematically illustrates the insertion of a cannula into the uterine horn by the method herein.

The method herein is described in regard to the accompanying drawings. Although the method herein can be practiced on most mammals, including humans, cattle, horses, sheep, hogs, dogs and cats, it will be herein described for simplicity, and not meant to be limiting, in relation to and as practiced on cattle. The method is practiced in an analogous manner on other mammals. FIG. 1 schematically illustrates a uterus of a cow and surrounding organs related to the uterus and reproductive system of a cow. FIG. 1 also illustrates the location of an incision made in the vaginal wall during the method herein. FIG. 2 schematically illustrates the positioning of a cannula for introducing the embryo to the recipient mammal.

An embryo for use as an embryo transplant in the method herein can be obtained from a donor mammal by any technique which removes an embryo or egg from a mammal. Many techniques have been developed or are being developed relating to removing intact and viable embryos or eggs from the uterus or ovaries of mammals. Such techniques include surgical and nonsurgical techniques. Exemplary of surgical techniques for removing embryos and eggs from host mammals is disclosed in U.S. Pat. No. 3,854,470 of Augspurger, which is incorporated herein by this reference. The surgical technique therein disclosed comprises surgically dissecting an oviduct and flushing the uterine horn and oviduct with a sterile solution for washing the embryo out of the uterine horn or oviduct. The oviduct is dissected in a location depending upon the number of days after ovulation of the donor animal. The embryo or egg is found in the oviduct in different locations depending on the time period after ovulation of the donor animal.

An egg collected from a donor mammal can be inseminated in the host animal or inseminated outside of the host animal. For the purposes of the method herein either in vivo or in vitro insemination of the egg obtained from the donor mammal can be used. For simplicity herein, the term "embryo" is used synonymously with the term "fertilized egg," "fertilized ovum," "morula," "blastocyst" or "expanded blastodermic vesicle."

Nonsurgical embryo removal techniques are also useful for supplying an embryo transplant. A technique for nonsurgically recovering an egg or embryo consists of using a flexible Foley catheter which has an inflatable balloon on one end and provides means for two directional fluid flow. The catheter is inserted in the vagina through the cervix, past the palpable division of the uterine horns into the horn adjacent to the ovary having a corpus luteum. After the catheter has been inserted, the balloon is inflated, blocking the flow of fluid out of the cervical end of the horn. The fluid is able to return through the catheter. While the horn is blocked at the other end by manually holding off the end of the horn closest to the ovary, the horn is flushed several times with a suitable medium introduced through the catheter, such as a phosphate buffered saline solution which provides a suitable environment for fertilized eggs.

After the embryo has been removed from the donor animal it is necessary to select a recipient mammal which will host the embryo transplant and carry the embryo through a normal gestation period terminating with the birth of the animal.

The method herein is for the implanting of an embryo transplant into a recipient mammal. To implant an embryo transplant a recipient mammal is selected whose estrus is synchronized with the donor mammal's estrus. That is, the recipient mammal's estrus is synchronized within a variation of plus or minus two days with the estrus of the donor mammal. Synchronization of estrus between two mammals can be controlled chemically as described in the aforementioned U.S. Pat. No. 3,854,470. The recipient mammal is examined to determine the ovary containing the corpus luteum. The corpus luteum is a reddish yellow mass of endocrine tissue that forms in the mammalian ovary in which an egg has been provided for fertilization. The ovaries can be rectally palpated to determine which ovary has the corpus luteum.

After determining which ovary has the corpus luteum formed thereon, an incision is made in the lateral wall of the vagina of the recipient mammal. With reference to FIG. 1 the incision is made in the lateral wall of the vagina posterior of the cervix. The incision is made using standard surgical instruments, such as a scalpel, properly sterilized. The incision can be a straight slit of up to about ¾ of an inch long or can be a partially circular or elliptical incision of the vaginal wall providing about ¾ of an inch opening.

The size of the incision is sufficiently large to provide access for a cannula to be inserted therethrough. Preferably, the size of the incision is sufficiently small that the incision is self-healing. A size of up to about ¾ of an inch for the incision is preferred as a longer incision generally will necessitate possible suturing to aid in the healing of the incision.

After the incision in the vaginal wall has been made, the uterine horn leading to the ovary having the corpus luteum thereon, is positioned proximate to the incision in the vaginal wall. The uterine horn of the uterus is sufficiently long and has sufficient flexibility that it can be maneuvered by rectal palpation proximally to the incision in the vaginal wall as shown in FIG. 2. In smaller mammals the uterine horn can be positioned using instruments. The uterine horn is positioned such that the wall of the uterine horn is exposed through the incision on the vaginal wall.

Using the incision in the vaginal wall as an opening to expose the wall of the uterine horn, a hole is punctured through the wall of the uterine horn. The hole can be punctured in the wall of the uterine horn using a surgical needle. Generally, a surgical needle of about 14 gauge or smaller provides a hole of the proper size. It is preferred to use a 16 gauge surgical needle as the hole provided by a 16 gauge needle is sufficiently large to enable insertion of an embryo and is sufficiently small to promote self-healing. The surgical needle is sterilized to prevent introduction of infection. As illustrated in FIG. 2, a cannula is inserted through the incision in the vaginal wall, through the hole in the wall of the uterine horn and into the lumen of the uterine horn. The embryo transplant from the donor mammal is introduced into the lumen of the the uterine horn through the cannula. The cannula can be any tubular instrument capable of being sterilized and of introducing the embryo into the uterine horn. For example, the cannula can be glass or plastic having a smooth pointed end for inserting through the punctured hole in the wall of the uterine horn. The cannula is preferably made of glass, as in the art of cannula manufacturing plastic cannulas are currently too thick. However, if plastic cannulas of the proper size to avoid damaging the endometrium are available they can be used. Preferably, the cannula is about the same gauge as the punctured hole, i.e., about 14 gauge or smaller and preferably about 16 gauge. The cannula used for inserting the embryo into the lumen of the uterine horn can be an insemination pipette which is curved at one end for facilitating insertion of the pipette into the vagina and uterine horn. However, it is preferred to use a straight cannula as the location of the end of the straight cannula can be readily determined so as to avoid damaging the delicate endometrium. After the embryo has been inserted into the lumen of the uterine horn, the cannula is withdrawn. The uterine horn then is allowed to return to its normal position. The hole in the wall of the uterine horn and the incision in the vaginal wall generally self-heal with the passage of time. If the hole in the vaginal wall was incised too large for self-healing or if it does not self-heal within a desired time, then sutures can be made to close the incision.

In the event that the recipient mammal has a corpus luteum formed upon both of its ovaries, then an embryo can be implanted within both of the respective uterine horns leading to the two ovaries. The implanting of two such embryo transplants into a recipient mammal results in the production of twins. Such twinning can be preferred to increase animal production on a relatively small amount of land. When embryo transplants are to be inserted into both of the uterine horns of a recipient mammal, either one incision or two incisions in the vaginal wall can be made. Preferably, one incision is made in the vaginal wall posterior of the cervix. The incision is made such that both of the two uterine horns can be rectally palpated and manipulated to place each uterine horn proximate to the incision.

The method herein allows implanting of an embryo transplant without affecting the cervix and the bulk of the endometrium. Generally, with nonsurgical embryo transplanting techniques wherein a catheter is inserted past the cervix, some damage to the cervix and endometrium can occur with the possible consequence that the cervix and endometrium are unable to support the embryo during gestation whereupon abortion of the embryo can result. Generally, nonsurgical techniques involve insertion of the embryo into the uterus with the aid of an instrument through the cervix of the uterus. Since the implanting procedure generally is done when the cow is in the sixth to the fourteenth day of the estrus cycle and preferably on about the seventh day for highest viability, such instrumental insertion through the cervix can cause excessive hemorrhaging which creates an atmosphere in which the embryo cannot survive. The method described herein leaves the cervix and bulk of the endometrium unaffected and is generally nondeleterious to the reproductive tract of the recipient mammal. Additionally, the method herein does not require the total anesthetizing of the recipient mammal. The method can be practiced without the need for anesthesia in regard to many mammals such as cattle, horses, sheep, hogs and the like. Therefore, especially in cattle, the method reduces the inherent dangers of general anesthesia for the recipient animal.

The method herein can be readily practiced with regard to farm animals at the location of the farm and thereby avoids the necessity of transporting such animals to an operating room site. The method herein can be practiced with minimal opportunity for inducing infection in the recipient mammal using sterile surgical instruments as only small incisions in the mammal are necessary. The method herein also provides economical advantages over current surgical techniques as less time is consumed, less people are required and elaborate surgical conditions such as operating rooms, anesthesia and the like are not required.

The method herein can be practiced on most mammals, including humans. Generally, the method is especially useful in transplanting bovine embryos, horse embryos, sheep embryos and hog embryos. The method also has applicability to domestic animals such as dogs and cats.

What is claimed is:

1. A method for implanting an embryo transplant from a donor mammal into the uterus of a recipient mammal, the method comprising the steps of:
    (a) positioning the uterine horn in the peritoneal cavity proximate to the vaginal wall;
    (b) inserting a cannula through the vaginal wall, through the wall of the uterine horn and into the lumen of the uterine horn of the recipient mammal;
    (c) introducing an embryo transplant into the lumen of the uterine horn through the cannula; and
    (d) withdrawing the cannula.

2. A method as recited in claim 1 wherein the cannula is inserted through the vaginal wall at a position posterior of the cervix.

3. A method as recited in claim 1 wherein the cannula is a straight cannula.

4. A method as recited in claim 1 wherein the cannula is smaller than about 14 gauge.

5. A method for implanting an embryo transplant from a donor mammal into the uterus of a recipient mammal, the method comprising the steps of:
    (a) making an incision in the lateral wall of the vagina of a recipient mammal posterior of the cervix;
    (b) positioning a uterine horn leading to an ovary having a corpus luteum thereon in proximity to the incision in the vaginal wall for exposing the wall of the uterine horn through the incision;
    (c) puncturing a hole through the exposed wall of the uterine horn;
    (d) inserting a cannula through the incision in the vaginal wall, through the hole in the wall of the uterine horn and into the lumen of the uterine horn;
    (e) introducing an embryo transplant into the lumen of the uterine horn through the cannula; and
    (f) withdrawing the cannula.

6. A method as recited in claim 5 wherein the incision made in the lateral wall of the vagina is a straight line incision.

7. A method as recited in claim 5 wherein the incision made in the lateral wall of the vagina is a circular incision.

8. A method as recited in claim 6 or 7 wherein the incision in the lateral wall of the vagina is about $\frac{3}{4}$ inch long.

9. A method as recited in claim 5 or 6 or 7 wherein the incision is of sufficient size to allow insertion of a cannula and is sufficiently small to be self-healing.

10. A method as recited in claim 5 wherein the uterine horn is positioned proximate to the incision on the vaginal wall by rectal palpation.

11. A method as recited in claim 5 wherein the hole is punctured through the wall of the uterine horn with a surgical needle.

12. A method as recited in claim 11 wherein the surgical needle is smaller than about 14 gauge.

13. A method as recited in claim 5 wherein the cannula is a straight cannula.

14. A method as recited in claim 5 wherein the cannula is smaller than about 14 gauge.

15. A method as recited in claim 5 wherein the recipient mammal, the donor mammal and embryo are bovine animals.

16. A method as recited in claim 5 wherein the donor and recipient mammals are horses.

17. A method as recited in claim 5 wherein the donor and recipient mammals are sheep.

18. A method as recited in claim 5 wherein the donor and recipient mammals are hogs.

19. A method as recited in claim 1 wherein the uterine horn is positioned proximate to an incision through the vaginal wall by rectal palpation.

* * * * *